(12) United States Patent
Marquardt et al.

(10) Patent No.: US 11,558,261 B2
(45) Date of Patent: Jan. 17, 2023

(54) NETWORK DEVICE AND MEDICAL SYSTEM FOR THE DETECTION OF AT LEAST ONE NETWORK PROBLEM

(71) Applicant: Drägerwerk AG & Co. KGaA, Lübeck (DE)

(72) Inventors: Klaus Marquardt, Lübeck (DE); Hannes Molsen, Lübeck (DE); Harald Schurack, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 0 days.

(21) Appl. No.: 17/369,508

(22) Filed: Jul. 7, 2021

(65) Prior Publication Data

US 2022/0014440 A1 Jan. 13, 2022

(30) Foreign Application Priority Data

Jul. 8, 2020 (DE) ...................... 10 2020 117 984.7

(51) Int. Cl.
*G06F 15/173* (2006.01)
*H04L 41/14* (2022.01)
*G16H 40/67* (2018.01)
*G16H 40/20* (2018.01)
*G16H 70/20* (2018.01)
*H04L 9/40* (2022.01)

(52) U.S. Cl.
CPC ............ *H04L 41/14* (2013.01); *G16H 40/20* (2018.01); *G16H 40/67* (2018.01); *G16H 70/20* (2018.01); *H04L 63/083* (2013.01)

(58) Field of Classification Search
None
See application file for complete search history.

(56) References Cited

U.S. PATENT DOCUMENTS 10,205,803 B1 2/2019 Sharifi Mehr
11,134,090 B1 * 9/2021 Swackhamer ........ H04L 63/145
(Continued)

FOREIGN PATENT DOCUMENTS

DE 102007024720 A1 12/2007
DE 102010045256 A1 5/2011
(Continued)

*Primary Examiner* — Brian Whipple
*Assistant Examiner* — Gregory P Tolchinsky
(74) *Attorney, Agent, or Firm* — McGlew and Tuttle, P.C.

(57) ABSTRACT

A network device (100) detects a network problem in a medical system (105). A reception module (110) receives current medical system process data. A monitoring module (120) detects predefined events (124) based on the process data and triggers a detection signal (132) output in the presence of a predefined event. A sending module (130) sends the detection signal to a predefined device address (134) via a network (140). The predefined events include: a predefined plurality of unsuccessful password entry attempts within a predefined first time period; an unsuccessful encryption within an encryption protocol framework; a predefined plurality of outputs via the network triggered via the network within a predefined second time period; an output of a signal, which is to be carried out, has been unsuccessful; and a predefined number of messages have been received within the framework of a service discovery within a predefined third time period.

17 Claims, 4 Drawing Sheets

(56) References Cited

U.S. PATENT DOCUMENTS

| | | | | |
|---|---|---|---|---|
| 2013/0132109 | A1* | 5/2013 | Mruthyunjaya | G16H 70/60 |
| | | | | 705/2 |
| 2013/0159504 | A1* | 6/2013 | Tang | H04L 41/0213 |
| | | | | 709/224 |
| 2014/0077956 | A1 | 3/2014 | Sampath et al. | |
| 2014/0266713 | A1* | 9/2014 | Sehgal | G08B 23/00 |
| | | | | 340/540 |
| 2017/0083929 | A1* | 3/2017 | Bates | G06F 16/951 |
| 2018/0278464 | A1 | 9/2018 | Donovan et al. | |
| 2020/0134165 | A1 | 4/2020 | Boodaei | |

FOREIGN PATENT DOCUMENTS

| | | |
|---|---|---|
| DE | 102015009087 A1 | 1/2017 |
| DE | 102010010949 B4 | 6/2018 |
| EP | 3813072 A1 | 4/2021 |
| KR | 20150007966 A | 1/2015 |

\* cited by examiner

NETWORK DEVICE AND MEDICAL SYSTEM FOR THE DETECTION OF AT LEAST ONE NETWORK PROBLEM

CROSS REFERENCE TO RELATED APPLICATIONS

This application claims the benefit of priority under 35 U.S.C. § 119 of German Application 10 2020 117 984.7, filed Jul. 8, 2020, the entire contents of which are incorporated herein by reference.

TECHNICAL FIELD

The present invention pertains to a network device for the detection of at least one network problem in a medical system. The present invention pertains, furthermore, to a medical system with at least one network device, to a process for the detection of at least one network problem in a medical system and to a computer program with a program code for carrying out such a process.

TECHNICAL BACKGROUND

It is known that a medical device outputs a corresponding warning message when a network problem is detected by the medical device. Furthermore, the forwarding of an alarm signal to alarm generators is known. Thus, DE 10 2015 009 087 A1 describes a regional and chronological assignment of alarm signals by an alarm source to a plurality of alarm generators.

SUMMARY

An object of the present invention is to provide an improved network device, especially a network device with improved forwarding of information in case of the detection of at least one network problem.

A network device for the detection of at least one network problem in a medical system with a reception module, with a monitoring module and with a sending module is provided according to the present invention to accomplish this object.

The reception module is configured to receive current process data of at least one process being carried out within the medical system.

The monitoring module is configured to detect the presence of a number of predefined events on the basis of the process data, and it is further configured to trigger a corresponding detection signal in the presence of at least one predefined event.

The sending module is configured to send the detection signal via a network connected to the network device to a predefined device address, especially to a predefined receiving device. The number of predefined events comprises here at least one of the following events: a predefined plurality of password entry attempts have been unsuccessful within a predefined past first time period; an encryption has been unsuccessful within the framework of an encryption protocol used in the network; a predefined plurality of outputs via the network have been triggered within a predefined past second time period; an outputting of a signal, which was to be carried out, has been unsuccessful; a predefined number of messages within the framework of a service discovery has been received within a predefined past third time period.

It was found within the framework of the present invention that an alarm generation in the presence of a network problem at a medical device does not reach the group of addressees relevant for the repair of this network problem or at least it does reach them only indirectly. It is therefore provided according to the present invention that when a network problem is detected, such a detection signal shall be sent to a predefined receiving device within the network, which receiving device is preferably located in the vicinity in space of a correspondingly trained person.

As a result, the operation of the medical system is not preferably interrupted or interfered with by the detection of the network problem. In particular, a distraction of the professional staff by an optical or acoustic output of the message about a network problem is avoided during the treatment of a patient by a medical professional staff.

The predefined events from the list of possible predefined events indicate different possible network problems. The sending of the detection signal via the sending module thus indicates according to the present invention the at least suspected presence of a network problem.

Furthermore, the network device according to the present invention makes possible a proper elimination of the network problem. In particular, the person competent for the network problem can be contacted with a short time delay due to the automated forwarding of the detection signal to the receiving device, especially to the mobile receiving device. Furthermore, due to the automated forwarding of the detection signal, the competent person can estimate especially well how quickly the network problem must be eliminated. As a result, the procedure of a possible elimination of this problem can be determined, for example, on the basis of an internally assigned urgency status, already shortly after the detection of the network problem.

The process data are according to the present invention data that indicate details of the process being carried out within the medical system, especially individual process steps, e.g., log entries of the medical system.

Modules of the network device according to the present invention may be arranged in a common housing or at least partially in separate housings. As an alternative or in addition, at least parts of the network device may be arranged in a common housing with parts of the medical system. The network device may be configured according to the present invention separately from the medical system and only access data of the medical system, for example, the process data. As an alternative or in addition, the network device may be a part of the medical system.

The modules of the network device may be configured by a common processor, and they are separated from one another according to the present invention at least at the software level.

The detection of the presence of one of the predefined events takes place according to the present invention on the basis of the process data. The detection may be based here, for example, on a detection of a predefined process step description indicated by the process data, of a predefined process signature indicated by the process data, of a predefined term within a process description indicated by the process data or the like.

The number of predefined events preferably comprises at least two of the above-mentioned events. The number of predefined events may comprise according to the present invention each non-empty subset of the above-mentioned set of events.

According to the present invention, the receiving device is not a part of the network device. It is preferably arranged separately in space from the network device.

The predefined device address is preferably a predefined server address of the receiving device predefined for the corresponding notification.

The network, with which the network device communicates, may be both a local network, for example, a hospital network, and a global network, which allows a communication with devices outside the hospital. Thus, the receiving device may be, for example, a receiving device of a service technician, who is located at a location separated in space from the medical system. For example, the receiving device may be a mobile receiving device, e.g., a mobile phone, a PC, a tablet, a smartwatch or the like.

Preferred embodiments of the network device according to the present invention will be described below.

In an especially preferred embodiment, the current process data comprise the corresponding protocol files for the at least one process being carried out within the medical system. Protocol files are in this sense, for example, log entries of the medical system. Process data, which are typically outputted by the medical system anyway, in order to log the process sequence, are preferably used in this embodiment. As a result, the network device according to the present invention can be integrated in an existing medical system in an especially simple manner.

In an especially advantageous embodiment, the sending of the detection signal to the predefined receiving device takes place in an automated manner within the communication protocol being used, especially via a Simple Network Management Protocol Trap (SNMP Trap). The use of such an SNMP Trap is known, in principle, for the communication within networks. The exact structure of such a communication will not therefore be discussed below in detail.

In an especially preferred embodiment, the monitoring module is configured to detect the presence of at least one physiological event from a number of predefined physiological events on the basis of a received number of measured values, especially physiological measured values, and to trigger a corresponding alarm generation signal as a function of this detection. The sending module is preferably configured here to send the alarm generation signal to at least one predefined alarm generation device via a network connected to the network device. The predefined receiving device is especially preferably different here from the at least one predefined alarm generation device. Distinction is especially advantageously made in this exemplary embodiment between the alarm generation via an alarm generation device and a notification via the receiving device for the presence of a predefined event that indicates a network problem. A distinction is made in this exemplary embodiment between alarm generation device and receiving device, so that a distinction is also made concerning the two groups of addressees between the patient-indicated alarm generation and the network-indicated notification.

The network device according to the present invention is preferably a medical device. It is especially advantageous for such a medical device that the detection of a network problem leads to a separate receiving device being contacted, which may be associated, for example, with a system administrator, with a service technician, or with another IT specialist for the medical device.

The detection signal preferably indicates the detected event from the number of predefined events.

In one embodiment of the network device according to the present invention, the number of predefined events is formed by exactly one event. The detection signal already indicates the corresponding event on the basis of the only one possible triggering event. The network device is advantageously configured in this embodiment for the detection of a single concrete network problem. As a result, the analysis of the detection signal is especially simple.

The predefined plurality of unsuccessful password entry attempts preferably comprises at least two attempts, especially at least 5 attempts, and especially preferably more than 5 attempts. The first time period comprises less than 10 minutes, especially less than 5 minutes, and especially preferably at most 2 minutes.

The predefined triggered plurality of outputs via the network preferably comprise at least 50, especially at least 75, especially preferably at least 100 outputs. The second time period comprises less than 5 minutes, especially less than 2 minutes, and especially preferably at most 30 sec.

The predefined number of messages within the framework of a service discovery preferably comprises at least 50 messages, especially at least 75 messages, and especially preferably at least 100 messages. The third time period preferably comprises less than 30 sec, especially less than 10 sec, and especially preferably less than 6 sec.

The network device is configured in an advantageous embodiment not to send a second detection signal for a predefined time interval after sending a first detection signal if the second detection signal is triggered by the detection of the same predefined event as was the first detection signal. It is avoided in this embodiment that the group of addressees for the notification according to the present invention about the presence of a network problem receive the same notification multiple times for the same network problem. A system administrator, a service technician, an IT specialist or the like is prevented hereby from being distracted several times based on the same event. It is only after the predefined time interval has elapsed that the corresponding group of addressees is alerted again to the presence of the corresponding network problem, i.e., to the detection of a predefined event, by the detection signal, i.e., in this case by the second detection signal. It is advantageously ensured hereby that a receipt of the first detection signal will not be forgotten. A second or additional detection signal is preferably sent then independently from the predefined time interval if another predefined event different from the predefined event that had led to the first detection signal was detected. The monitoring module is preferably configured to block the second detection signal when the same predefined event is detected corresponding to this embodiment until the predefined time interval has expired. In an alternative and/or additional variant of this embodiment, the sending module is configured to block the second detection signal when the same predefined event is detected corresponding to this embodiment until the predefined time interval has expired. The predefined time interval in this embodiment is preferably at least 10 minutes, especially at least 30 minutes, and especially preferably at least 2 hours.

According to a second aspect of the present invention, a medical system with at least one network device according to at least one of the above exemplary embodiments and with the receiving device is proposed to accomplish the above-mentioned object, wherein the receiving device is connected to the network device via the network.

The medical system according to the present invention comprises the network device according to the present invention and therefore has all the advantages of the network device according to the present invention.

The network is, for example, a hospital network, in which a plurality of medical devices are connected to one another. Such a hospital network is typically managed by a system administrator or by another IT specialist. The receiving device is preferably associated with such a system administrator or with such an IT specialist, in order for the notification for indicating the presence of a network problem to have an address suitable for the elimination of this network problem.

The receiving device is preferably a mobile receiving device. The person responsible for receiving the detection signal can be informed thereby of the network problem during his usual activity, which may involve, for example, a change of location. This is especially advantageous because such a network problem is typically a rare event in such a network.

In an advantageous embodiment, the predefined receiving device is a management module of a central network management unit of the medical system. Such a management module is advantageously associated with a specialist for the management of such a network structure, so that the notification according to the present invention by the network device has an addressee suitable for the elimination of the network problem.

In an especially preferred embodiment, the medical system has the at least one predefined alarm generation device. As a result, an alarm generation can be triggered at the alarm generation device on the basis of measured values, for example, physiological measured values, in the presence of a predefined physiological event. In a variant of this embodiment, the at least one predefined alarm generation device is arranged separately in space from the predefined receiving device. As a result, an alarm generation via the alarm generation device has a different group of addressees than the notification according to the present invention via the receiving device.

In an especially advantageous embodiment, the detection of the presence of at least one predefined event from the number of predefined events does not trigger an output at a medical device configured for the treatment or the examination of a patient. Medical professional staff is prevented hereby from being distracted during the treatment of the patient by an acoustic or visual output of the medical device based on the detected network problem. The medical professional staff is not typically trained nor does it have the necessary time to solve such a network problem with the use of the medical device. This embodiment makes it therefore advantageously possible for the medical professional staff to focus on its medical activity and on specifically notifying the professional staff competent for the network via the receiving device in the presence of a network problem.

The receiving device is preferably arranged separately in space from patients to be treated by the medical system. As a result, neither is the patient disturbed when a network problem is detected, nor is the attending medical professional staff disturbed by the receiving device. The receiving device is preferably configured to generate an output when it receives the detection signal according to the present invention. Such an output is not advantageously disturbing in this embodiment for a group of people located in the vicinity of the patient being treated.

According to a third aspect of the present invention, a process for detecting at least one network problem in a medical system is proposed for accomplishing the above-mentioned object. The process according to the present invention has the following steps:
receipt of current process data of at least one process being carried out within the medical system;
detection of the presence of a number of predefined events on the basis of the process data;
triggering of a corresponding detection signal in the presence of at least one predefined event; and
sending of the detection signal via a network connected to the network device to a predefined device address, especially to a predefined receiving device,
wherein the number of predefined events comprises at least one of the following events: A predefined plurality of password entry attempts have been unsuccessful within a predefined past first time period; an encryption within the framework of an encryption protocol used in the network has been unsuccessful; a predefined number of outputs via the network have been triggered within a predefined past second time period; an output of a signal, which is to be carried out, has been unsuccessful; and a predefined number of messages have been received within the framework of a service discovery within a predefined past third time period.

The process according to the present invention is carried out by the network device according to the present invention, so that it has all the advantages of the network device according to the first aspect of the present invention.

In an especially preferred embodiment, the process according to the present invention has, furthermore, the following steps:
detection of a physiological event from a number of predefined physiological events based on a received number of measured values, especially of physiological measured values;
triggering of a corresponding alarm generation signal as a function of this detection; and
sending of the alarm generation signal via a network connected to the network device to at least one predefined alarm generation device, wherein the predefined receiving device is different from the at least one predefined alarm generation device, especially at a location separated in space from the at least one predefined alarm generation device.

The process according to the present invention makes it possible in this embodiment to provide two different groups of addressees, namely, a group of addressees with an alarm generation device, which generates an alarm on the basis of physiological events, and a group of addressees with a receiving device, which is notified on the basis of process data, which indicate a possible network problem. The group of addressees for which an alarm is to be generated preferably comprises a medical professional staff, whereas the group of addressees to be notified comprises a system administrator, service staff, IT specialist or the like.

According to a fourth aspect of the present invention, a computer program with a program code for carrying out a process according to the present invention according to one of the above embodiments when the program code is executed on a processor or on a programmable hardware component is proposed. A plurality of steps of the process according to the present invention are preferably carried out by a common computer, by a common processor or by a common programmable hardware component. The individual steps are preferably separated here from one another at least at the software level by corresponding software blocks. All steps of the process according to the present invention are especially preferably carried out on a common computer, on a common processor or on a common programmable hardware component.

The present invention shall now be explained in more detail on the basis of advantageous exemplary embodiments schematically shown in the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
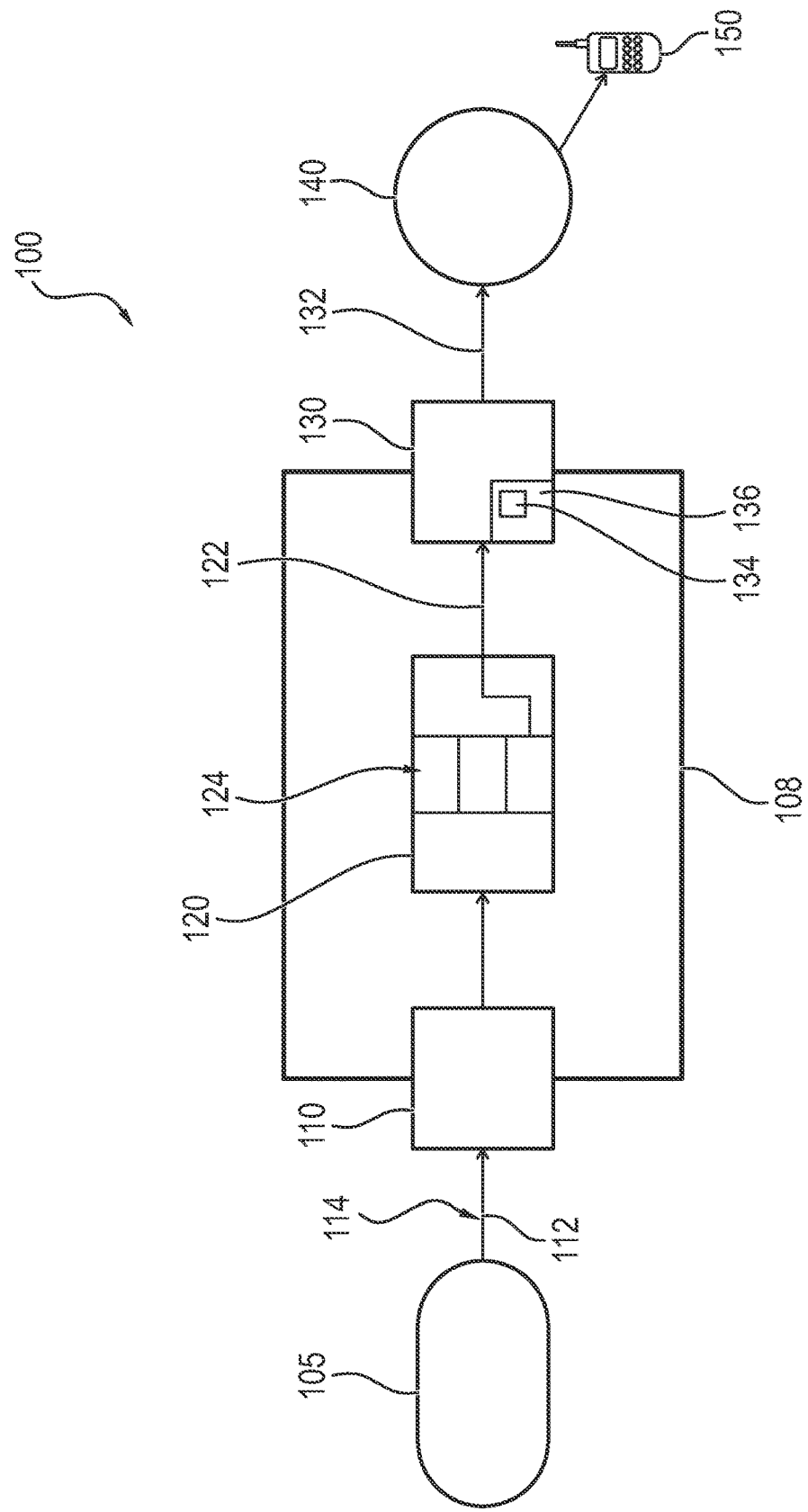
FIG. 1 is a schematic view of a first exemplary embodiment of a network device according to a first aspect of the present invention.

Referring to the drawings, FIG. 1 shows a schematic view of a first exemplary embodiment of a network device 100 according to a first aspect of the present invention.

The network device 100 is configured for detecting at least one network problem in a medical system 105. It comprises for this a reception module 110, a monitoring module 120 and a sending module 130. The network device 100 is not a part of the medical system 105 in the exemplary embodiment being shown. The communication between the medical system 105 and the network device 100 takes place through a communication channel with the reception module 110. This communication channel may be a part of the network 140, to which the network device 100 is connected. As an alternative or in addition, the communication channel with the medical system 105 may be a direct, wired or wireless communication channel.

The reception module 110 is configured to receive current process data 112 of at least one process carried out within the medical system 105. In the exemplary embodiment shown, the process data 112 are log entries of a medical device which are carried out within the medical system 105. The reception module 110 converts the current process data 112, which it receives through a data signal 114 from the medical system 105, into data that can be processed for the monitoring module 120, and it forwards these to the monitoring module 120. Such a conversion may also comprise an identical forwarding of the process data.

The monitoring module 120 is configured to detect the presence of a number of predefined events 124 on the basis of the process data 112. The monitoring module 120 is configured, in particular, to analyze the process data 112 in a predefined manner in order to detect the presence of an event from a predefined group of events. Such an analysis may be carried out by an analysis of a word, of a signature, of a sequence of characters or the like within the process data 112. Finally, the monitoring module 120 is further configured to trigger an output of a corresponding detection signal 132 in the presence of at least one such predefined event 124. The triggering of the detection signal 132 is carried out via a triggering signal 122, which is outputted to the sending module 130.

The predefined events 124 being monitored by the monitoring module 120 comprise at least one of the following events: A predefined plurality of password entry attempts have been unsuccessful within a predefined past first time period; an encryption within the framework of an encryption protocol used in the network has been unsuccessful; a predefined plurality of outputs via the network have been triggered within a predefined past second time period; an output of a signal, which output is to be carried out, has been unsuccessful; and a predefined number of messages have been received within the framework of a service discovery within a predefined past third time period.

The following three predefined events 124 are monitored in the exemplary embodiment being described: A predefined plurality of password entry attempts have been unsuccessful within a predefined past first time period; an encryption within the framework of an encryption protocol used in the network has been unsuccessful; a predefined number of messages have been received within the framework of a service discovery within a predefined past third time period.

The unsuccessful encryption is especially an unsuccessful Transport Layer Security Handshake (TLS Handshake), which forms a reliable sign of an existing network problem.

The predefined past first time period is preferably less than 10 minutes, especially less than 5 minutes, and especially preferably at most 2 minutes. The predefined plurality of password entry attempts equal preferably at least three, especially at least five and especially preferably more than five.

The sending module 130 is configured to send the detection signal 132 via the network 140 connected to the network device to a predefined device address 134, especially to a predefined receiving device 150. The device address is stored here in a memory 136 of the sending module 130. In an alternative or additional exemplary embodiment, the predefined device address is stored outside the sending module and within the network device, for example, within the monitoring module.

The receiving device 150 is the terminal associated with the device address 134. The predefined device address 134 is, for example, a server address, an IP address or the like of the receiving device 150. The receiving device 50 is a mobile terminal here, such as a mobile phone or the like. The sending of the detection signal 132 takes place in an automated manner within the communication protocol being used, especially via a Simple Network Management Protocol Trap (SNMP Trap). Examples of a possible implementation of such an SNMP Trap are known to the person skilled in the art and will not therefore be explained below.

The network device 100 has here, in addition, a housing 108, which protects the modules of the network device 100 from external effects.

The network 140 is a hospital network in this case. Different medical devices are interlinked with one another via the hospital network. At least one of these medical devices is contained in the medical system 105, which provides the process data 112 for the network device 100 according to the present invention.

The modules of the network device 100 are preferably connected to one another in a wired manner. The modules may be formed here by a common processor of the network device 100, and they are separated from one another at least at the software level.

Figure 2:
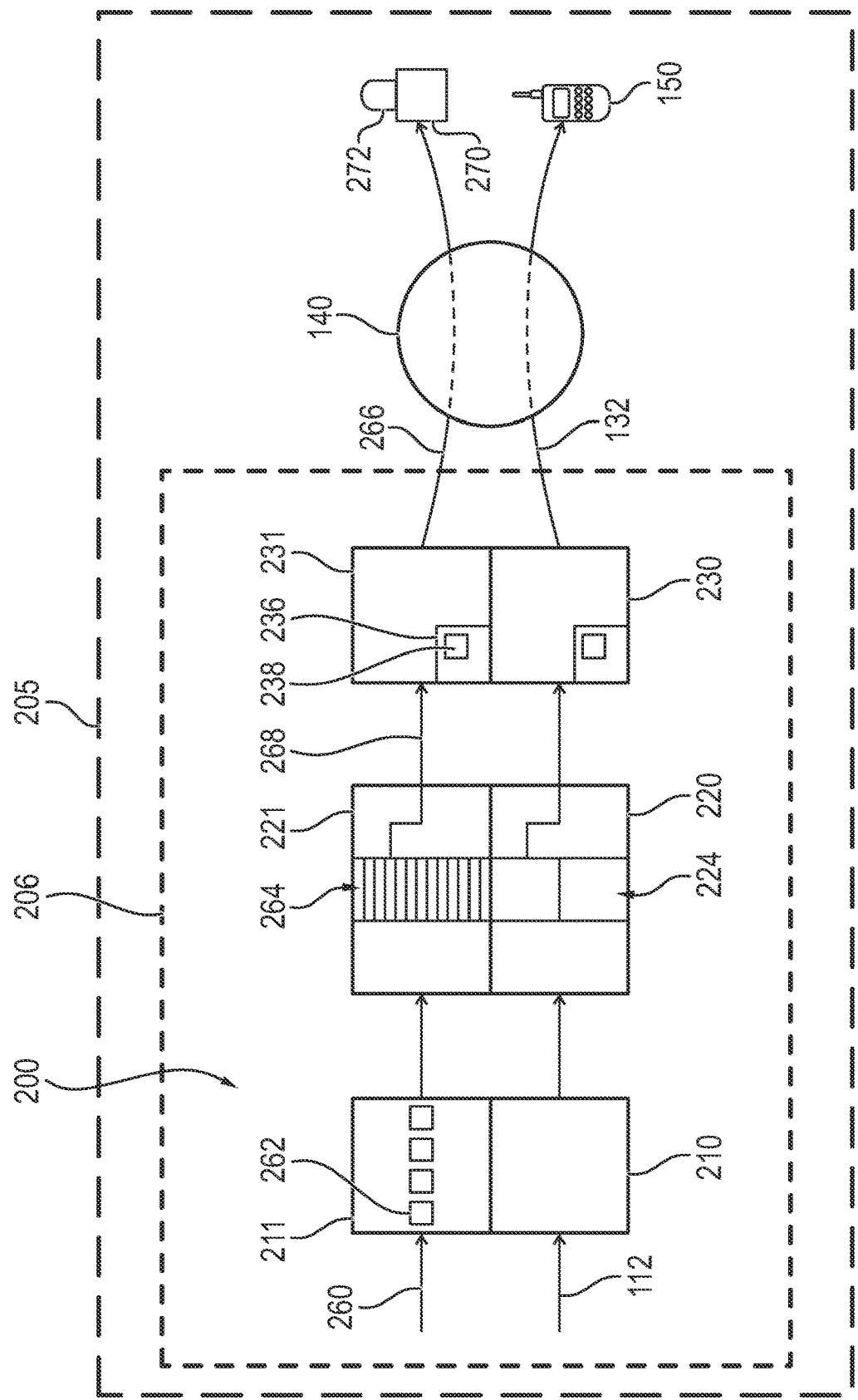
FIG. 2 is a schematic view of a second exemplary embodiment of the network device according to the first aspect of the present invention.

FIG. 2 shows a schematic view of a second exemplary embodiment of the network device 200 according to the first aspect of the present invention.

The network device 200 differs from the network device 100 shown in FIG. 1 in that it forms a part of the medical system 205. The process data 112 are thus sent within the medical system 205 in order to reach the reception module 210. The reception module 210 has an additional receiving area 211, which is configured to receive measured value data 260, which indicate a number of measured values 262, especially a number of physiological measured values. The process data 112 are received in the exemplary embodiment by the reception module 210 via an interface that is different from the interface via which the measured value data 260 are received. In an alternative or additional exemplary embodiment, for example, in the exemplary embodiment shown in FIG. 3, these data can be received via a common interface.

The monitoring module 220 correspondingly has an additional monitoring area 221, which is configured to detect the presence of at least one physiological event from a number of predefined physiological events 264. The number of predefined physiological events 264 is greater than the number of predefined events 224, which indicate a network problem. This is due to the fact that many different events affecting the patient, which are indicated by measured values, especially by physiological measured values, may occur during the treatment of a patient.

If such a physiological event is detected, the monitoring module 220 with the additional monitoring area 221 is configured to trigger an alarm generation signal 266, which is outputted by the sending module 230. The triggering of the alarm generation signal 266 is brought about by an additional triggering signal 268.

The sending module 230 correspondingly has an additional sending area 231, which is configured to send the alarm generation signal 266 after the receipt of the output signal 268, and this alarm generation signal 266 is sent via the network 140 connected to the network device to at least one predefined alarm generation address 238, which indicates a corresponding alarm generation device 270. The alarm generation device 270 is different here from the predefined receiving device 150. The alarm generation address 238 is stored in a memory 236 of the sending module 230.

The receiving device 150 and the alarm generation device 270 are likewise respective parts of the medical system 205. The receiving device 150 and the alarm generation device 270 are arranged separated in space from one another. The receiving device 150 is preferably located at a location that is intended for the management of the IT infrastructure of a facility having the medical system, e.g., of a hospital or of a nursing home. The receiving device 150 is preferably separated in space from a person being treated by the medical system 205. The addressee for the detection signal indicating a network problem, namely, a system administrator, a service technician, an IT specialist or the like, is not located typically in an area around the patient being treated. An output triggered by the detection signal 132 does not therefore need to take place in the area around the patient being treated. The alarm generation device 270 is preferably located, by contrast, in the vicinity of a medical professional staff, e.g., in a room for nursing staff. In the exemplary embodiment shown, the alarm generation device 270 is a device with a light 272, which provides an optical output after receipt of the alarm generation signal 266 via the network 140.

The detection signal 132 is sent exclusively to the receiving device 150 in the exemplary embodiment shown. In one exemplary embodiment, not shown, the detection signal is sent to a group of receiving devices, e.g., to a group of receiving devices that are assigned to a group of service technicians.

The alarm generation signal 266 is outputted exclusively to the alarm generation device 270 in the exemplary embodiment shown. In one exemplary embodiment, not shown, the alarm generation signal is sent to a group of alarm generation devices, e.g., to a group of mobile devices, which are each associated with a respective medical professional staff.

In the exemplary embodiment shown the network device 200 is a part of a medical device 206, e.g., of a ventilator, of a patient monitor, of a patient monitoring device or the like.

The predefined events 224 being monitored by the monitoring module 220 comprise at least one of the following two events: A predefined plurality of password entry attempts have been unsuccessful within a predefined past first time period, and an encryption within the framework of an encryption protocol has been unsuccessful.

The monitoring module 220 in the exemplary embodiment being shown is further configured not to send a second detection signal over a predefined time period after sending the first detection signal 132 if the second detection signal is triggered by detection of the same predefined event 224 as the first detection signal 132. The predefined time period equals here at least 10 minutes, preferably at least 30 minutes, and especially preferably at least 2 hours. The network problem is prevented hereby from leading to a constant notification of the receiving device 150, which recurs at short time intervals. The first detection signal 132 is defined in the sense of the present invention as a detection signal that is to be sent chronologically before the second detection signal.

Figure 3:
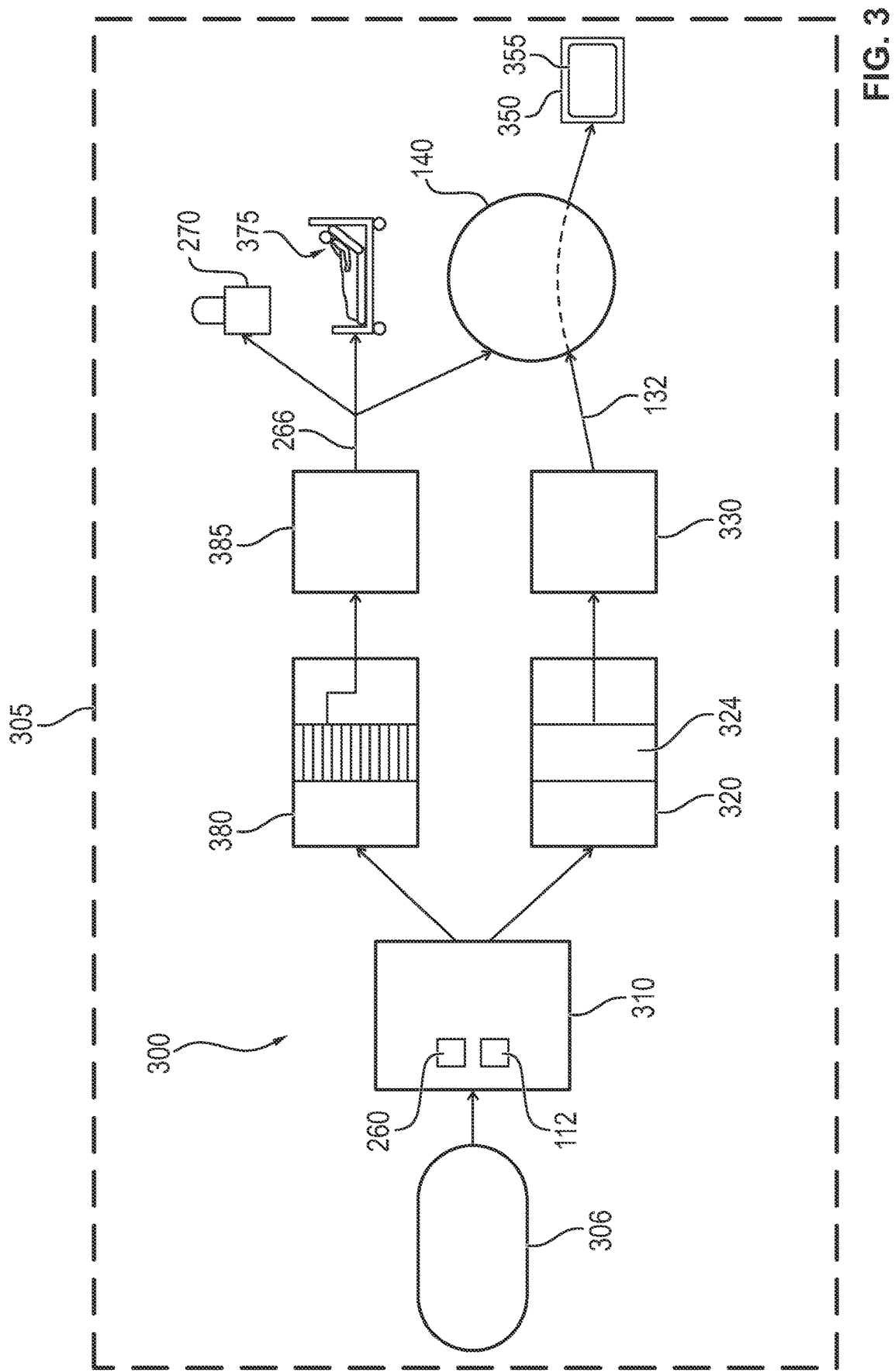
FIG. 3 is a schematic view of an exemplary embodiment of a medical system according to a second aspect of the present invention.

FIG. 3 shows a schematic view of an exemplary embodiment of a medical system 305 according to the second aspect of the present invention.

The medical system 305 differs from the medical system 205 from FIG. 2 in that the reception module 310 receives data, which comprise both process data 112 and measured value data 260, from a medical device 306, The reception module 310 is configured to determine from the received data the process data 112 and to forward them to the monitoring module 320, and, in addition, to determine from the received data the measured value data 260 and to send them to a separate alarm generation monitoring module 380. The alarm generation monitoring module 360 operates in exactly the same manner as the additional monitoring area 221 of the monitoring module 220 from FIG. 2. The monitoring module 320 differs from the monitoring modules 120, 220 described so far in that the monitoring module 320 monitors only the occurrence of a single predefined event 324, namely, of the event that a predefined plurality of password entry attempts have been unsuccessful within a predefined past first time period. In an alternative exemplary embodiment, not shown, only the event that an encryption has been unsuccessful within the framework of an encryption protocol used in the network is monitored. In yet another alternative exemplary embodiment, not shown, only the event that a predefined plurality of outputs have been triggered via the network within a predefined past second time interval is monitored. In yet another alternative exemplary embodiment, not shown, only the event that a predefined number of messages have been received within the framework of a service discovery within a predefined past third time period is monitored. The predefined number of messages preferably comprises more than 50, especially more than 75, and especially preferably more than 100 messages. The third time interval is preferably shorter than 30 sec, especially shorter than 10 sec, and preferably shorter than 6 sec.

Furthermore, the medical system 305 with the network device 300 according to the present invention is distinguished by the fact that an alarm generation sending module 385 is configured separately from the sending module 330. The sending module 330 is configured corresponding to the sending module 130 from FIG. 1, and the receiving device 350 in this exemplary embodiment is a management module of a central network management unit of the medical system 305. The management module has a display 355 here as an output medium.

The alarm generation sending module 385 is configured to send the corresponding alarm generation signal 266 directly to the alarm generation device 270. Furthermore, the alarm generation signal 266 is sent to an output unit in the vicinity of the patient 375 and is outputted to the network 140. The output to the network 140 ensures that alarm generation systems possibly used within the corresponding hospital can access the alarm generation signal 266 via the network. Such a general storage in the network 140 is not provided for the notification of the receiving device 350 by the detection signal 132, but only a specific notification of the receiving device 350 is provided in order to specifically inform the predefined group of addressees of the probably present network problem.

The detection signal 132 is not preferably sent to a medical device configured for the treatment or examination of the patient 375 or it does not at least trigger an output at this medical device. It is avoided hereby that medical professional staff will be distracted by information that can lead to a more rapid elimination of the network problem in another group of addressees, e.g., the system administrator.

The alarm generation monitoring module 380 and the alarm generation sending module 385 are modules separated in space from the network device in the exemplary embodiment shown. In one exemplary embodiment, not shown, the two modules are separated in space from the corresponding monitoring module and from the corresponding sending module of the network device but they nevertheless form a part of the network device according to the present invention. In another exemplary embodiment, not shown, the two modules are corresponding parts of the monitoring module and of the sending module of the network device according to the present invention.

Figure 4:
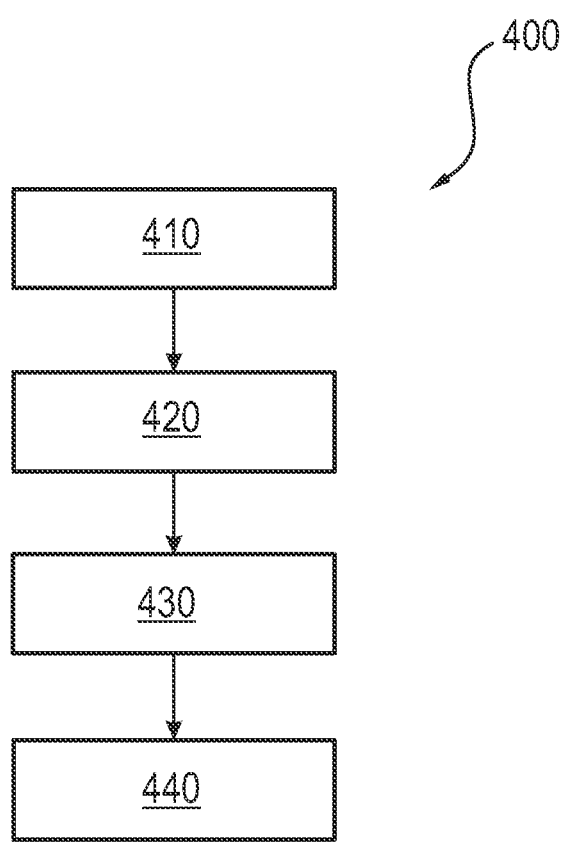
FIG. 4 is a flow chart of an exemplary embodiment of a process according to a third aspect of the present invention.

FIG. 4 shows a flow chart of an exemplary embodiment of a process 400 according to a third aspect of the present invention.

The process 400 according to the present invention is configured for the detection of at least one network problem in a medical system. It has for this purpose the process steps described below.

A first step 410 comprises a receipt of current process data of at least one process carried out within the medical system.

A next step 420 comprises a detection of the presence of a number of predefined events on the basis of the process data. The number of predefined events comprises here according to the present invention at least one of the following events: A predefined plurality of password entry attempts have been unsuccessful within a predefined past first time period; an encryption within the framework of an encryption protocol used in the network has been unsuccessful; a predefined plurality of outputs via the network have been triggered within a predefined past second time period; an output of a signal, which is to be carried out, has been unsuccessful; and a predefined number of messages have been received within the framework of a service discovery within a predefined past third time period.

The next step 430 comprises a triggering of a corresponding detection signal in the presence of at least one predefined event.

A final step 440 comprises the sending of the detection signal via a network connected to the network device to a predefined device address, especially to a predefined receiving device.

Steps 410, 420, 430 and 440 are preferably carried out in this order. Step 410 leads to the further steps of the process 400 only if a predefined event is detected on the basis of the process data received in step 410. Step 420 is always carried out within the framework of such a detection and steps 430 and 440 are always carried out in this order after such a detection. After the detection signal has been triggered in step 430, the sending of the detection signal to the predefined device address is carried out immediately in step 440.

Since the above-mentioned possible predefined events indicate a network problem, they typically occur rarely, so that step 420, namely, the detection of a predefined event, takes place only rarely following step 410.

After sending the detection signal corresponding to step 440, this step 440 is not carried out preferably any longer for a predefined time interval if the last detection signal was triggered by a detection of the same predefined event as the detection signal to be sent currently. The predefined time interval preferably equals at least 10 minutes, especially preferably at least 30 minutes, and especially at least 2 hours.

The steps of the process 400 are complemented by the following process steps in an especially preferred exemplary embodiment:
- detection of a physiological event from a number of predefined physiological events on the basis of a received number of measured values, especially of physiological measured values;
- triggering of a corresponding alarm generation signal dependent on this detection; and
- sending of the alarm generation signal via a network connected to the network device to at least one predefined alarm generation device, wherein the predefined receiving device is different from the at least one predefined alarm generation device, especially separated in space from the at least one predefined alarm generation device.

Distinction is made in this preferred exemplary embodiment between two different groups of addressees for different outputs. An alarm generation via the alarm generation signal reaches a first group of addressees, which is present in the area of the alarm generation device. A notification about the detection signal reaches, by contrast, a second group of addressees, which is present in the area of the receiving device, which is different from the alarm generation device. The first group of addressees preferably comprises medical professional staff, whereas the second group of addressees preferably comprises a system administrator, service staff, an IT specialist or the like. It is therefore ensured in this preferred exemplary embodiment that the network problem will not distract the medical professional staff, which is not typically trained to eliminate the network problem, but the network problem rapidly and reliably reaches an addressee suitable for eliminating this network problem.

While specific embodiments of the invention have been shown and described in detail to illustrate the application of the principles of the invention, it will be understood that the invention may be embodied otherwise without departing from such principles.

LIST OF REFERENCE NUMBERS 100, 200, 300 Network device
105, 205, 305 Medical device
206, 306 Medical device
108 Housing
110, 210, 310 Reception module
112 Process data
114 Data signal
120, 220, 320 Monitoring module
122 Triggering signal
124, 224, 324 Predefined events
130, 230, 330 Sending module
132 Detection signal
134 Device address
136, 236 Memory
140 Network
150, 350 Receiving device
211 Additional receiving area
221 Additional monitoring area
231 Additional sending area
238 Alarm generation address
260 Measured value data
262 Measured value
264 Physiological events
266 Alarm generation signal
268 Additional triggering signal
270 Alarm generation device
272 Light
355 Display
375 Patient
380 Alarm generation monitoring module
385 Alarm generation sending module
400 Process
410, 420, 430, 440 Process steps

What is claimed is:

1. A network device for detecting at least one network problem in a medical system, the network device comprising:
a reception module having a processor configured to receive current process data of at least one process carried out within the medical system;
a monitoring module having a processor configured to detect a presence of a number of predefined events based on the process data, and which is further configured to trigger an output of a corresponding detection signal in a presence of at least one of the number of predefined event, the monitoring module being configured to detect a presence of at least one physiological event, from a number of predefined physiological events, based on a received number of measured values and to trigger a corresponding alarm generation signal depending on this detection, the alarm generating signal being separate from the detection signal; and
a sending module having a processor configured to send the detection signal, via a network connected to the network device, to a predefined device address, the predefined device address corresponding to a predefined receiving device, the sending module being configured to send the alarm generation signal via the network connected to the network device to at least one predefined alarm generation device; the predefined receiving device being different from the at least one predefined alarm generation device, the alarm generation signal not being sent to the predefined receiving device, the detection signal not being sent to the predefined alarm generation device,
wherein the number of predefined events comprises at least one of the following events:
a predefined plurality of password entry attempts that have been unsuccessful within a predefined past first time period;
an encryption within the framework of an encryption protocol used in the network having been unsuccessful;
a predefined plurality of outputs via the network having been triggered within a predefined past second time period;
an output of a signal, which is to be carried out, having been unsuccessful; and
a predefined number of messages having been received within the framework of a service discovery within a predefined past third time period.

2. A network device in accordance with claim 1, wherein the process data includes current process data comprising corresponding protocol files for the at least one process carried out within the medical system.

3. A network device in accordance with claim 1, wherein:
the predefined device address corresponds to a predefined receiving device; and
the sending of the detection signal to the predefined receiving device is automated within a communication protocol used via a Simple Network Management Protocol Trap.

4. A network device in accordance with claim 1, wherein the network device is configured to not send a second detection signal for a predefined time interval after sending a first detection signal if the second detection signal is triggered by the detection of the same predefined event as the first detection signal.

5. A medical system comprising:
a receiving device having a predefined device address, the receiving device being connected to a network;
at least one network device being connected to the receiving device via the network, the least one network device comprising:
a reception module having a processor configured to receive current process data of at least one process carried out within the medical system;
a predefined alarm generation device arranged separated in space from the receiving device;
a monitoring module having a processor configured to detect a presence of a number of predefined events based on the process data, and which is further configured to trigger an output of a corresponding detection signal in a presence of at least one of the number of predefined event, the monitoring module being configured to detect a presence of at least one physiological event, from a number of predefined physiological events, based on a received number of measured values and to trigger a corresponding alarm generation signal depending on this detection, the alarm generating signal being separate from the detection signal; and
a sending module having a processor configured to send the detection signal, via a network connected to the network device, to a predefined device address, the sending module being configured to send the alarm generation signal via the network to the predefined alarm generation device, the predefined receiving device being different from the predefined alarm generation device, the alarm generation signal not being sent to the predefined receiving device, the detection signal not being sent to the predefined alarm generation device, wherein the number of predefined events comprises at least one of the following events: a predefined plurality of password entry attempts that have been unsuccessful within a predefined past first time period; an encryption within the framework of an encryption protocol used in the network having been unsuccessful; a predefined plurality of outputs via the network having been triggered within a predefined past second time period; an output of a signal, which is to be carried out, having been unsuccessful; and a predefined number of messages having been received within the framework of a service discovery within a predefined past third time period.

6. A medical system in accordance with claim 5, wherein the predefined receiving device is a management module of a central network management unit of the medical system.

7. A medical system in accordance with claim 5, wherein a detection of a presence of at least one predefined event from the number ofpredefined events does not trigger an output at a medical device configured for the treatment or examination of a patient.

8. A medical system in accordance with claim 5, wherein the receiving device is arranged separated in space from patients to be treated by the medical system.

9. A medical system in accordance with claim 5, wherein the process data includes current process data comprising corresponding protocol files for the at least one process carried out within the medical system.

10. A medical system in accordance with claim 5, wherein the sending of the detection signal to the predefined receiving device is automated within a communication protocol used via a Simple Network Management Protocol Trap.

11. A medical system in accordance with claim 5, wherein:
the monitoring module is configured to detect a presence of at least one physiological event, from the number of predefined physiological events, based on a received number of measured values and to trigger a corresponding alarm generation signal depending on this detection; and
the sending module is configured to send the alarm generation signal via the network connected to the network device.

12. A medical system in accordance with claim 5, wherein the network device is configured to not send a second detection signal for a predefined time interval after sending a first detection signal if the second detection signal is triggered by the detection of the same predefined event as the first detection signal.

13. A process for detecting at least one network problem in a medical system, the process comprising the steps of:
receiving current process data of at least one process carried out within the medical system;
detecting by a monitoring device a presence of a number of predefined events based on the process data;
triggering a corresponding detection signal based on a presence of at least one predefined event of the number of predefined events;
sending the detection signal via a network connected to the network device to a predefined device address, wherein the number of predefined events comprises at least one of the following events:
a predefined plurality of password entry attempts have been unsuccessful within a predefined past first time period;
an unsuccessful encryption within a framework of an encryption protocol used in the network;
a predefined plurality of outputs via the network have been triggered within a predefined past second time period;
an unsuccessful output of a signal which is to be carried out;
a predefined number of messages within the framework of a service discovery has been received within a predefined past third time period;
detecting by the monitoring device a physiological event from a number of predefined physiological events based on a received number of measured values;
triggering a corresponding alarm generation signal as a function of this detection; and
sending of the alarm generation signal via the network connected to the network device to at least one predefined alarm generation device, wherein the predefined device address corresponds to a predefined receiving device and the predefined receiving device is different from the at least one predefined alarm generation device and is separated in space from the at least one predefined alarm generation device.

14. A process in accordance with claim 13, wherein a computer program with a program code carries out at least some of the process steps when the program code is executed on a computer, on a processor or on a programmable hardware component.

15. A process in accordance with claim 13, wherein:
the predefined device address corresponds to a predefined receiving device; and
the sending of the detection signal to the predefined receiving device is automated within a communication protocol used via a Simple Network Management Protocol Trap.

16. A process in accordance with claim 13, wherein the network device is configured to not send a second detection signal for a predefined time interval after sending a first detection signal if the second detection signal is triggered by the detection of the same predefined event as the first detection signal.

17. A process in accordance with claim 13, wherein:
the alarm generating signal is separate from the detection signal;
the alarm generation signal is not sent to the predefined receiving device, the detection signal is not sent to the predefined alarm generation device.

* * * * *